United States Patent [19]

Clemente et al.

[11] Patent Number: 5,552,436
[45] Date of Patent: Sep. 3, 1996

[54] PROCESS FOR TREATING HEMANGIOMA

[75] Inventors: Emmett Clemente, Manchester; Robert W. Mendes, Dedham; Aloysius O. Anaebonam, Burlington; Mumtaz Ahmed, Westford, all of Mass.

[73] Assignee: Ascent Pharmaceuticals, Inc., Billerica, Mass.

[21] Appl. No.: 415,712

[22] Filed: Apr. 3, 1995

[51] Int. Cl.$^6$ .................................................. A61K 31/35
[52] U.S. Cl. .............................................. 514/456
[58] Field of Search ............................... 514/456

[56] References Cited

U.S. PATENT DOCUMENTS

| | | | |
|---|---|---|---|
| 4,271,182 | 6/1981 | Sullivan | 424/283 |
| 4,362,742 | 7/1982 | Sullivan | 424/283 |

FOREIGN PATENT DOCUMENTS

| | | | |
|---|---|---|---|
| A1-0587264 | 3/1994 | European Pat. Off. | A61K 31/35 |

OTHER PUBLICATIONS

Habif, T. P., ed., Clinical Dermatology: A Color Guide to Diagnosis and Therapy, 2nd Ed., The C. V. Mosby Co. (St. Louis, Mo: 1989), pp. 582–585.

Brauenwald et al., eds., Harrison's Principals of Internal Medicine, 11th Ed., McGraw–Hill Book Co. (New York: 1990), pp. 1043, 1161, and 1958.

*Primary Examiner*—Marianne M. Cintins
*Assistant Examiner*—William R. A. Jarvis
*Attorney, Agent, or Firm*—Welsh & Katz, Ltd.

[57] ABSTRACT

A process and pharmaceutical composition for treatment of hemangioma in humans is disclosed. The pharmaceutical composition comprises a chromone compound of the following formula, or a pharmacologically acceptable salt, ester or amide thereof:

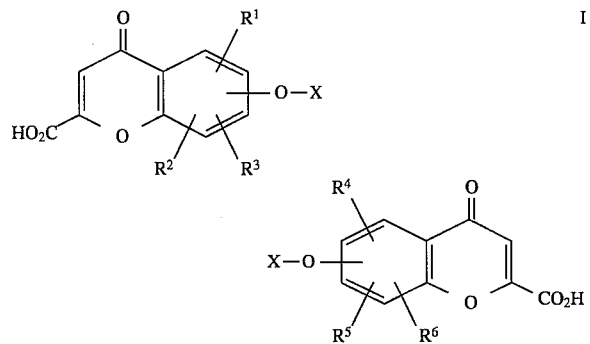

dissolved or dispersed in a pharmacologically acceptable carrier. In accordance with the process, a therapeutically effective amount of the composition is topically administered to a hemangioma of a human patient.

11 Claims, No Drawings

PROCESS FOR TREATING HEMANGIOMA

DESCRIPTION

1. Technical Field

This invention relates to the treatment of hemangioma, and more particularly to a composition and process for treating hemangioma that utilizes a chromone compound of the general formula shown in formula I, hereinafter, wherein $R^1$, $R^2$, $R^3$, $R^4$, $R^5$ and $R^6$ i.e. $R^1$–$R^6$ and X are defined hereinafter.

2. Background of Invention

A Compound of formula I, hereinafter, and its pharmacologically acceptable salts, esters and amides has been used successfully in the treatment of asthma for many years. One particular compound, commonly known as cromolyn, is routinely used as a prophylatic treatment for asthma, rhinitis, conjunctivitis and intestinal mastocytosis.

Cromolyn is not a bronchial or vasodilator as is usual for asthma treatments. Rather, cromolyn acts to inhibit the release of inflammatory mediators such as histamine from several types of cells. Inhalation of a solution containing the disodium salt of cromolyn, (cromolyn sodium), on a regular schedule by an individual suffering from asthma provides a prophylactic treatment for bronchial asthma. The prophylactic response increases with the length of use of the drug.

A chromone compound corresponding to formula I and its pharmacologically acceptable salts, esters and amides has also been reported to be effective against certain allergic skin disorders such as atopic eczema and various skin conditions that involve skin mast cells and/or an antibody-antigen reaction. (Sullivan U.S. Pat. Nos. 4,362,742 and 4,271,182), as well as being affective against allergic conditions of the eye. However, the effectiveness of these compounds against other conditions of the skin or epidermis is not predictable.

The exact mechanism of action of a chromone compound is unknown. A chromone compound is believed to possess no vasodilator, antihistaminic or anti-inflammatory activity, although it may possess anti-angiogenic properties. It is known that a chromone compound, and particularly cromolyn, is poorly absorbed by the lungs and by the gastrointestinal tract. Only about 7–8 percent of a usual total dose is absorbed from the lung, and is then rapidly excreted, unchanged, in the bile or urine. The remainder is expelled from the nose or, if swallowed, excreted by the alimentary tract.

Hemangioma is caused by localized dilation of blood vessels. There is also some indication that hemangioma may involve angiogenesis, the creation of additional blood vessels and capillaries in the affected area. Hemangiomas that occur in the skin result in discoloration of the skin (usually red, sometime blue) and can also form a nodular, protrubant, compressible mass on the surface of the skin. Although the lesions are blood filled and can hemorrhage, most hemangiomas are completely benign and cause no physical damage. At times a particular hemangioma grows very rapidly resulting in swelling of the affected areas, or threatens to compromise certain structures, such as the eyes, auditory canals or airways.

Most hemangiomas are present at birth or appear within the first year of life. Hemangioma lesions are present in about 6–8 percent of children. Usually only one lesion is present, although several can occur. In a usual progression, the lesion enlarges for several months, remaining stable for a period of time, and finally spontaneously regresses, or involutes. There is rarely permanent scarring left by the regression of the lesion.

If the lesion is small and stable it has been generally recommended that the lesion remain untouched to permit spontaneous regression. Treatment has generally only been recommended when the lesion is growing rapidly and/or when the lesion interferes with vital structures such as the eyes, auditory canals, or airways.

If treatment with a medicament is indicated, prednisone (2–4 mg/kg/day) is given in a divided dose twice daily. At this dosage, most lesions stabilize and markably regress in 2 to 4 weeks. The dosage is then reduced to a single dose and tapered off to every other day for a few weeks and then discontinued. At times a stronger dose or second course of treatment is needed.

An intralesion injection of a corticosteroid has also been used successfully for certain lesions, but oral steroids have been preferred.

Steroid treatment of hemangioma lesions has the usual side effects associated with steroid treatments. For this reason, treatment of the lesion is not indicated or recommended in most circumstances.

In some cases, when there is no response to steroid treatment, and the lesion continues to threaten vital structures or if the lesion does not regress by late childhood, the lesion is evaluated for surgical removal. Surgical removal of the lesion involves the usual risks associated with an invasive procedure, including a risk of scarring.

Certain types of hemangiomas are not operable and in some instances are treated with lasers to cauterize the vessels involved in the lesion. Laser treatments result in epidermal damage and can result in scarring.

Although there are generally no adverse physiological effects of hemangioma, there are psychological effects caused by peer teasing and ridicule regarding the skin discoloration. It would therefore be advantageous to be able to successfully treat hemangioma lesions without the possible side effects of steroid treatment or surgery. The disclosure that follows provides one such treatment.

SUMMARY OF INVENTION

A process for treating hemangioma is disclosed herein. This process utilizes topical administration of a formulation containing a lesion-reducing amount of a compound of formula I, or a pharmacologically acceptable salt, ester or amide thereof. The particularly preferred compound is commonly referred to as cromolyn [1,3-bis(2-carboxychromon-5-yloxy)-2-hydroxypropane] and is represented in formula II, hereinafter.

Surprisingly, it is found that topical treatment with cromolyn reduces the inflammation of the underlying vessels, causing the lesion to regress thereby eliminating the discoloration of the skin caused by the hemangioma. Topical cromolyn treatment may also slow or stop any angiogenic process that may be causing or contributing to the hemangioma lesion. This process of treatment results in early regression of the lesion with no known side effects. It can therefore be used on a great number of lesions, not merely those threatening harm to the patient.

The compound utilized in the present process as the active agent and hereinafter referred to as the "active agent" or "active ingredient", in the treatment conforms to the structure of formula I, below, and includes pharmacologically acceptable salts, esters and amides thereof where $R^1$, $R^2$, $R^3$, $R^4$, $R^5$ and $R^6$; i.e. $R^1$–$R^6$ and X are further defined hereinafter.

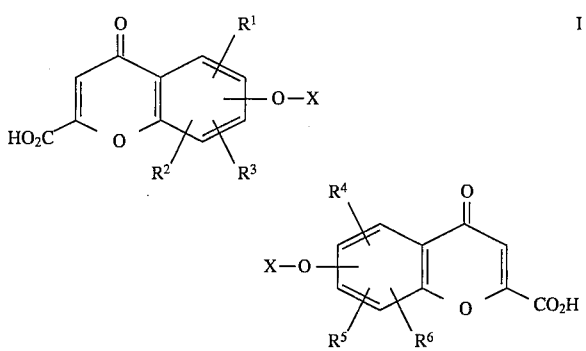

The molecule of formula I can be generally described as two chromone molecules linked by an O-X-O chain. In the above formula, and in all other formulas shown herein, hydrogen atoms that are not needed to show conformation about a particular bond are not shown.

Although $R^1$–$R^6$ can vary as fully described hereinafter, in general, it is preferred that no more than one of $R^1$, $R^2$ and $R^3$ and no more than one of $R^4$, $R^5$ and $R^6$ is other than hydrogen, and each is selected from a hydrogen, a halogen atom, a $C_1$–$C_6$ alkyl, hydroxy, $C_1$–$C_6$ alkoxy or substituted alkoxy group, and X is as defined hereinafter. More preferred compounds of formula I are those in which each of $R^1$–$R^6$ is hydrogen, and the carboxyl groups are present as alkali metal carboxylate salts.

The X group is preferably a straight or branched hydrocarbon chain containing 3 to 7 carbon atoms. The chain can be interrupted by one or more oxygen atoms. Even more preferably the chain is a polymethylene chain substituted by one or more hydroxyl groups, with a 2-hydroxy-trimethylene chain (—$CH_2CHOHCH_2$—) being a particularly preferred chain.

Although the above describes more preferred X groups, X can be one of a wide variety of groups as fully set forth hereinafter.

The structure of a particularly preferred compound of formula I is shown below as formula II, and is commonly known as cromolyn:

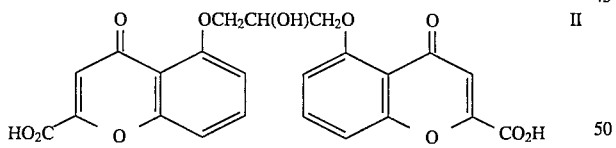

The most preferred derivative of formula II for use in the disclosed process is the disodium salt thereof, hereinafter referred to as cromolyn sodium.

A contemplated process comprises the administration to a human with hemangioma of a composition that contains a pharmacologically acceptable carrier having dissolved or dispersed therein a therapeutically effective (lesion-reducing) amount of a compound of formula I or a pharmacologically acceptable salt, ester or amide thereof, as an active ingredient or agent. That composition is topically applied to the hemangioma-afflicted area of the skin. The composition can be applied to the lesion several times a day and then either be covered or left open to the air. Exemplary therapeutically effective amounts, by weight, of the active ingredient can range from about 0.5 to about 10 percent of the total composition.

The present invention has several benefits and advantages.

One benefit is that use of the described process and composition can reduce or eliminate the lesions on the skin caused by hemangioma without adverse side effects such as can occur with a present steroidal process of treatment.

Another benefit is that the hemangioma lesion can be reduced or eliminated without the possibility of scarring that exists with surgical or laser procedures.

One advantage of the described process is that it can be used for most hemangioma lesions causing early regression of the lesion even where there is no immediate physical harm being caused or threatened.

Another advantage is that early regression of the lesion can greatly reduce or eliminate adverse psychological effects caused by peer teasing and ridicule for the deformity.

Further benefits and advantages of the invention will be apparent to those of skill in the art from the description that follows.

DETAILED DESCRIPTION OF THE INVENTION

The present invention contemplates a process for treatment of hemangioma. A contemplated process utilizes a compound corresponding to formula I, preferably the compound commonly known as cromolyn, (formula II) and more preferably the disodium salt of cromolyn, as an active agent compound in a composition that is topically administered to the hemangioma lesions of humans in need of such treatment; i.e., having hemangioma.

A. Compounds

A compound utilized in the present invention is represented by formula I.

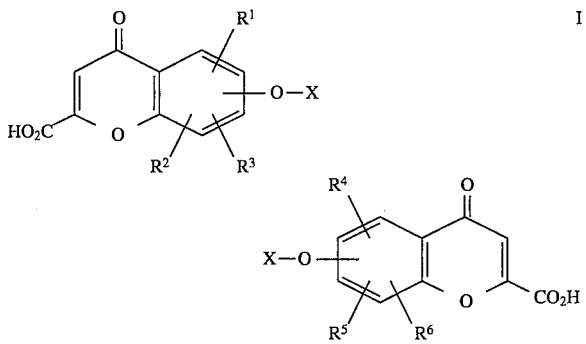

Each of $R^1$–$R^6$ can be the same, or different. Each $R^1$–$R^6$ can be a hydrogen; a halogen (halo) group or moiety (i.e. chloride, bromide, iodide or fluoride); a $C_1$–$C_6$ lower alkyl group (i.e. a methyl, ethyl, propyl, isopropyl, butyl, tertiary-butyl, or hexyl group); hydroxy; $C_1$–$C_6$ lower alkoxy (i.e. a methoxy, ethoxy, propoxy, isopropoxy, butoxy, tertiary-butoxy or hexyloxy group); substituted $C_1$–$C_6$ lower alkoxy group; or a substituted $C_1$–$C_6$ lower alkyl, as are discussed below.

The substituted lower alkyl or alkoxy group can be substituted with the following groups: hydroxyl; lower ($C_1$–$C_6$) alkoxy; carboxy or halo such as chloro-bromo-iodo- or fluoro-); $C_1$–$C_6$ lower alkenyl, e.g. allyl or methylallyl; benzyl; and nitro. A substituent group is not itself substituted. It is preferred that each $R^1$–$R^6$ be unsubstituted.

In general, it is preferred that no more than one of $R^1$, $R^2$ and $R^3$ and no more than one of $R^4$, $R^5$ and $R^6$ is other than hydrogen, and each is selected from a hydrogen, a halogen atom, a $C_1$–$C_6$ alkyl, hydroxy, $C_1$–$C_6$ alkoxy or substituted alkoxy group, and X is as defined before. A preferred compound is symmetric with $R^1$ being the same as $R^4$, $R^3$ being the same as $R^5$ and $R^2$ being the same as $R^6$. More preferred compounds of formula I are those in which each of $R^1$–$R^6$ is hydrogen.

The bridging X group of formula I is a saturated or unsaturated, substituted or unsubstituted, straight or branched polymethylene chain having between 3 and 10 carbon atoms can be interrupted by one or more carbocyclic rings or oxygen-containing heterocyclic rings, (e.g. benzene, dioxan, tetrahydrofuran, or dihydropyran rings), oxygen atoms or carbonyl groups.

The X group is preferably a straight or branched hydrocarbon chain containing 3 to 7 carbon atoms. The chain can be interrupted by one or more oxygen atoms. Even more preferably, the chain is a polymethylene chain substituted by one or more hydroxyl groups, with a 2-hydroxy-trimethylene chain ($-CH_2CHOHCH_2-$) being a particularly preferred chain. The structure of a particularly preferred compound of formula I is shown below as formula II, and is commonly known as cromolyn:

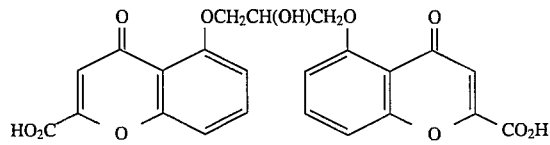

Although the above describes more preferred X groups, X can be one of a wide variety of groups as set forth hereinafter.

The X group can be a straight or branched, saturated or unsaturated hydrocarbon chain. Additionally, X can be such a chain interrupted by one or more oxygen atoms, carbonyl groups or carbocyclic or heterocyclic rings and can be substituted by one or more halogen atoms (e.g. chlorine, bromine, iodine or fluorine atoms), or hydroxy or $C_1$–$C_6$ lower alkoxy (e.g. methoxy, ethoxy, propoxy, isopropoxy, butoxy, tertiary-butoxy, etc.) groups. Some specific examples of the X group are groups of the following formulas:

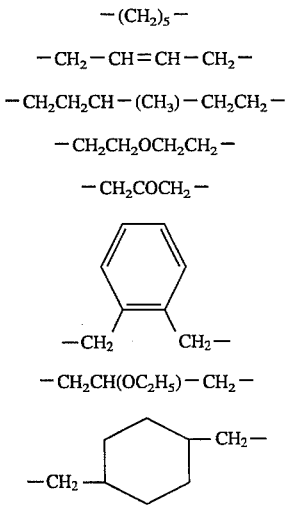

-continued $$-CH_2CH_2\overset{\overset{\displaystyle CH_2OH}{\mid}}{\underset{\underset{\displaystyle CH_2Cl}{\mid}}{C}}-$$

$-CH_2CHOHCH_2-$ $-CH_2CHOHCH_2OCH_2CHOHCH_2-$

Different or corresponding positions on the chromone molecules can be linked by the O-X-O chain, although symmetrical linkages are preferred.

Pharmacologically acceptable salts of a compound of formula I or formula II suitable for use in the disclosed process include for example, ammonium salts, alkali metal salts (e.g. sodium, potassium and lithium), alkaline earth metal salts (e.g. magnesium and calcium), and salts with organic amines (e.g. mono-, di- or tri-$C_1$–$C_6$-alkyl amines, piperidine, morpholine and trialkanol $C_1$–$C_6$-alkyl amine salts).

Pharmacologically acceptable esters include simple $C_1$–$C_6$ alkyl esters (e.g. methyl, ethyl, propyl, isopropyl, butyl, tertiary-butyl and hexyl esters). Pharmacologically acceptable amides include simple amides (for example amides with ammonia and $C_1$–$C_6$ lower alkylamines such as methylamine, ethylamine, and the like whose alkyl portions are discussed before) and more complex amides with amino acids, e.g. glycine.

Specific examples of compounds of formula I and derivatives thereof are provided in U.S. Pat. No. 4,362,742, whose disclosures are incorporated herein by reference.

The most preferred derivative of formula II for use in the disclosed process is the disodium salt thereof, hereinafter referred to as cromolyn sodium.

The phrase "pharmacologically acceptable" salts, esters and amides as used herein refers to non-toxic salts, esters and amides of formula I as discussed above.

B. Compositions

The compound of formula I or one of its pharmacologically acceptable salts, esters or amides dissolved or dispersed in a therapeutically effective amount in a pharmacologically acceptable carrier constitutes a composition (preparation) useful in a process of this invention. The disodium salt of a compound of formula II, where $R^1=R^2=R^3=R^4=R^5=R^6=H$, and $X=-CH_2CHOHC_2H-$, is preferred for use in treatment.

Although a compound of formula I and its pharmacologically salts, esters and amides can be administered as a pure chemical, it is preferred that it be administered as a pharmaceutical composition. In either event, a contemplated compound is administered in an amount sufficient to provide a therapeutically effective dose, as is discussed hereinafter.

Accordingly, the present invention utilizes a pharmaceutical composition comprising a therapeutically effective dose of a compound of formula I or a pharmacologically acceptable salt, esters or amide thereof, hereinafter referred to as the "active ingredient" or "agent", dissolved or dispersed in a pharmacologically acceptable carrier or diluent.

A therapeutically effective amount of a contemplated chromone compound of formula I typically constitutes about 0.5 to about 10.0 weight percent of a contemplated composition. More preferably, that amount is about 2.0 to about 6.0 weight percent.

A pharmaceutical composition is prepared by any of the process well known in the art of pharmacy all of which involve bringing into association the active ingredient and the carrier therefore. For therapeutic use, a compound utilized in the present invention can be administered in the form of conventional pharmaceutical compositions. Such compositions can be formulated so as to be suitable for topical administration of the active ingredient. In these compositions, the agent is typically dissolved or dispersed in a physiologically tolerable carrier or diluent.

A carrier or diluent is a material useful for administering the active compound and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and compositions that do not produce an allergic or similar untoward reaction when administered to a human.

The pharmacologically tolerable carrier can take a wide variety of forms suitable for topical administration, such as an ointment, water-miscible ointment, cream, lotion, paste, gel or liniment. These carriers can be aqueous, oily (oleaginous) or water-miscible or water-dispersible. They can be oil-in-water or water-in-oil based emulsions. A discussion of some types of suitable carriers is present in U.S. Pat. No. 4,362,742, whose disclosures are incorporated herein by reference.

The preferred carrier composition for the disclosed process is an oil-in-water emulsion in which the active ingredient is present in the water phase. The preferred oil-in-water emulsion is comprised of a water phase containing the active ingredient. Water is typically present at about 40 to about 80 weight percent and more preferably at about 66 to about 72 weight percent of the composition.

One or more water-miscible organic solvents such as glycerine, propylene glycol can also be present in the water phase. A sequestering agent such as edentate disodium dihydrate (EDTA) can also be present, as can a pH value-adjusting acid. Phosphoric acid is also preferably used in the water phase in an amount required to obtain the required necessary pH value.

The pH value can range between about 3.0 and about 8.0. The more preferred pH value range is about 4.0 to about 7.0. The most preferred pH value is 5.5.

Compound names used herein are usually used common names as well as those utilized in the *International Cosmetic Ingredient Dictionary*, The Cosmetic, Toiletry, and Fragrance Association, Washington, D.C. (1993), and *The U.S. Pharmacopeia, The National Formulary*, [USP XXII; NF XVII] United States Pharmacopeial Convention, Inc., Rockville, Md., 1990.

The oil phase is comprised of materials that individually can be solids or liquids at room temperature, e.g. about 20° C. These materials include waxes such as white wax and emulsifying wax, squalene and a silicone oil such as dimethicone. The oil phase also contains a component of the emulsifier, a $C_2$–$C_4$-acyl polypropyleneglycol (PPG) $C_{12}$–$C_{18}$ alkyl ether that contains an average of about 2–4 PPG groups per molecule. These materials impart an appropriate creamy feel to the composition upon the skin and tend to form an oleaginous layer over the treated hemangioma lesion.

A $C_{12}$–$C_{18}$ alcohol or mixtures thereof is also preferably present. Illustrative $C_{12}$–$C_{18}$ alcohols include lauryl, myristyl, cetyl, stearyl and oleyl alcohols.

The emulsifier includes emulsifying wax and preferably a mixture of two ingredients. The first is a $C_2$–$C_4$-acyl polypropyleneglycol (PPG) $C_{12}$–$C_{18}$ alkyl ether that contains an average of about 2–4 PPG groups per molecule. The second is a polyoxyethyleneglycol (PEG) $C_{14}$–$C_{26}$ ether having an average of about 8–17 PEG groups per molecule.

The emulsifying wax and the PEG compounds are preferably present together at about 8–12 weight percent of the total preparation, and in a weight ratio of about 15:1 to about 1:1, more preferably at about 10:1 to about 8:1, and most preferably about 9:1 in the order mentioned.

The ratio of the emulsifying wax and PEG emulsifier used is designed to provide a calculated HLB number of about 8 to about 14, and more preferably about 10 to about 12. The total amount of emulsifier used is typically a function of the total amount of oil phase ingredients, with more total emulsifier being used with a greater amount of oil phase ingredients, and less total emulsifier with the lower amount of oil phase ingredients, as is well known.

Emulsifying wax has an average HLB value of about 11. A particularly preferred PPG-containing emulsifier is PPG-2 myristyl ether propionate that has an HLB value of 11. A particularly preferred PEG-containing emulsifier is polyoxyethylene-10-oleyl ether that has an HLB value of 12.4. The above HLB value ranges are calculated based upon these emulsifiers.

PPG-2 myristyl ether propionate can be replaced with one of the compounds encompassed by the designation $C_2$–$C_4$ acyl-PPG(2–4) $C_{12}$–$C_{18}$ ether. Exemplary materials include PPG-3 lauryl ether butyrate and PPG-4 stearyl ether acetate, and the like. Similarly, PEG-10-oleyl ether (oleth-10; PEG compound) can be replaced with another PEG (7–12) $C_{14}$–$C_{20}$ alkyl ether such as PEG-12-cetyl ether (ceteth-12), PEG-7-stearyl ether (steareth-7), PEG-11-cetyl/stearyl ether (ceteareth-11), and the like.

It is noted that substitution in the PPG compound and PEG compound are considered together as these two compounds are present in the carrier in a combined total of 2–6 percent weight to weight with a weight to weight PPG-containing emulsifier to PEG-containing emulsifier ratio in the range of about 4:1–1:1, preferably about 3:1–2:1, most preferably of 2.5:1. This ratio results in the desired HLB number.

A contemplated preparation typically has a viscosity of a cream or ointment. Exemplary viscosities are thus about 20,000 to about 100,000 cps at 25° C., and more preferably about 50,000 to about 70,000 cps.

One and preferably more than one preservative is also preferably present in a commercial preparation. Exemplary preservatives include methylparaben, propylparaben and imidurea.

The following table provides a preferred range of weight to weight percentages for each particularly preferred ingredient present in a particularly preferred oil-in-water emulsion preparation for commercial use.

| Ingredient | % W/W Ranges |
| --- | --- |
| Cromolyn sodium | 0.5–10 |
| Emulsifying wax, N.F. | 8–17 total, in |
| Polyoxy-10 Oleyl Ether, N.F. (PEG) | a ratio of 8:1–10:1 |
| PPG-2 Myristyl Ether Propionate | for the wax: PEG, and a 4:1–1:1 ratio for PPG:PEG |
| Squalene, U.S.P. | 2–10 |
| White Wax, N.F. | 0.5–5 |
| Dimethicone, N.F. | 0.5–5 |
| Cetyl Alcohol, N.F. | 1–10 |
| Propylparaben, N.F. | 0.05–0.2 |
| Purified Water, U.S.P. | q.s. |

-continued

| Ingredient | % W/W Ranges |
|---|---|
| Glycerin, U.S.P. | 1–5 |
| Edetate Disodium Dihydrate, U.S.P. | 0.01–1 |
| Propylene Glycol, U.S.P. | 1–5 |
| Methylparaben, N.F. | 0.1–0.4 |
| Imidurea, N.F. | 0.1–0.3 |
| Phosphoric Acid, N.F. | q.s. |

Changes in the specific, particularly preferred, ingredients listed are contemplated. Thus one of ordinary skill in the art can substitute similar ingredients for those discussed above without substantially altering the effectiveness of the carrier and the final composition. The viscosity of carrier can be changed so long as it remains suitable for topical application.

In addition, if a certain ingredient is changed resulting in different hydrophilic/lipophilic balance (HLB), this can be compensated for, using known techniques, by changing another ingredient.

Specific examples of the acceptable alterations in the particularly preferred given ingredients are set forth below. Specific combinations of changes that result in acceptable compositions are easily determined by known procedures because "acceptability" arises mostly from emulsion characteristics rather than from a major change in drug availability.

Dimethicone is a mixture of fully methylated linear siloxane polymers end-blocked with trimethylsiloxy units. These materials are commercially available from several suppliers at varying viscosities ranging from about 0.65 to about centistokes 2,500,000, (Cst), with lower molecular weight polymers exhibiting the lower viscosities up to about a weight of about 30,000 and viscosity of about 1000 Cst, at which polymer chain entanglement occurs, resulting in a leveling in properties.

A preferred dimethicone utilized herein has a viscosity of about 100 to about 300 Cst, and more preferably about 150 to about 250 Cst. [1 Cst=1 cps.]

Cetyl alcohol can be substituted by $C_{12}$–$C_{18}$ alkyl such as lauryl, myristyl, and stearyl alcohols. Methylparaben and propylparaben can be substituted by $C_1$–$C_5$ alkyl paraben, or other suitable preservatives.

Any pharmacologically suitable acid can be used in place of phosphoric acid to adjust the pH of the composition.

Other compounds that can be used in place of squalene include acetylated lanolin. Substitutions for imidurea include DMDM Hydantoin. Emulsifying wax can be replaced with cetylalcohol:steareth-20 whereas stearamidopropyldimethyl amine can be used in place of white wax.

It should also be understood that in addition to the aforementioned carrier ingredients and substitutions, a pharmaceutical formulation described herein can include, as appropriate, one or more additional carrier ingredients such as buffers, binders, surface active agents, additional thickeners and preservatives (including antioxidants), lubricants, and the like. It is also contemplated that a penetration enhancer can be included to permit the active ingredient to penetrate the skin more effectively. One contemplated penetration enhancer is 2-n-nonyl-1,3-dioxolane, known as SEPA (Soft Enhancer for Percutaneous Absorption). SEPA can be used at about two weight percent (2 wt %) to about twenty weight percent (20 wt %). Fragrance and/or odor masking compounds can also be added.

Process

As noted earlier, a process for treating hemangioma is contemplated here. Broadly, a compound whose structure corresponds to that of formula I, or a pharmacologically acceptable salt, ester or amide thereof, as active ingredient, dissolved or dispersed in a pharmacologically acceptable carrier is topically administered (applied) to a hemangioma of a human patient. The compound is present in the composition in an amount sufficient to provide a therapeutically effective amount (a hemangioma lesion-reducing amount) of active ingredient compound over the period of administration. This amount ranges between about 0.02 g and about 0.4 g per treatment, and more preferably about 0.04 g to about 0.2 g per treatment.

The composition is administered by topically applying the composition to an area affected by the hemangioma. The site can then be covered, or left open to the air. This treatment can be repeated a plurality of times such as several times per day for 12 months, or until the hemangioma regresses and disappears.

The duration of a particular treatment can vary depending upon the size, type and severity of the hemangioma. Typical administration lasts about 3–6 months.

Administration is very easily carried out on an out-patient basis.

Efficacy of a contemplated process can be assessed by visual inspection of the patient's hemangioma lesion. The size and inflammation of the lesion typically begins to noticeably decrease after 1 month. Treatment is then continued until the lesion has disappeared.

EXAMPLE I

Exemplary Topical Preparation

A topical preparation for treating humans with hemangioma was prepared using the ingredients shown below for the preparation of 60 kilograms of a 4 percent cromolyn sodium cream.

| Ingredient | % W/W |
|---|---|
| Cromolyn sodium | 4.00 |
| Emulsifying wax, N.F. | 9.00 |
| PPG-2 Myristyl Ether Propionate | 2.50 |
| Polyoxy-10-Oleyl Ether, N.F. | 1.00 |
| Squalene, U.S.P. | 4.00 |
| White Wax, N.F. | 2.00 |
| Dimethicone, N.F. | 1.00 |
| Cetyl Alcohol, N.F. | 3.00 |
| Propylparaben, N.F. | 0.10 |
| Purified Water, U.S.P. | 68.80 |
| Glycerin, U.S.P. | 2.50 |
| Edetate Disodium Dihydrate, U.S.P. | 0.10 |
| Propylene Glycol, U.S.P. | 1.50 |
| Methylparaben, N.F. | 0.20 |
| Imidurea, N.F. | 0.30 |
| Phosphoric Acid, N.F. | q.s |
| pH value | 5.5 |
| Viscosity (25° c.) | 60,000 cps |

The cream is prepared by the following procedure. Percentage of total weight is given in parenthesis.

Step 1

Charge the main mixing kettle with 25.68K of purified water (42.80%) and heat to 75–80° C. Add 1.50K of glycerin (2.50%), 60 g of disodium EDTA U.S.P. (0.10%) and 900 g of propylene glycol (1.50%) individually while mixing at 30 rpm. Add 120 g of methylparaben N.F. (0.20%) and mix for 5 minutes at 30 rpm to disperse. Reduce speed to 20 rpm and mix for ½ hour.

Step 2

In a separate container, heat 5.40K of emulsifying wax N.F. (9.00%), 1.50K of PPG-2 myristyl ether propionate (2.50%), 600 g polyoxy-10 oleyl ether N.F. (1.00%), 2.40K squalene U.S.P. (4.00%), 1.20K white wax (2.00%), 600 g dimethicone N.F. (1.00%), 1.80K cetyl alcohol (3.00%) and 60 g propylparaben N.F. (0.10%) to 75°–80° C. Mix at 1700 rpm for 5 minutes.

Step 3

At 75°–80° C., add Step #2 to Step #1 with mixing at 40 rpm. Mix at 40 rpm speed for ½ hour.

Step 4

Cool evenly to 35°–40° C. over a 60 minute period with mixer at 20 rpm.

Step 5

Premix 600 g of purified water U.S.P. (1.00%) and 180 g of imidurea N.F. (0.30%) in a separate container at 250 rpm on the Dayton Gearmixer. Mix manually for 15 minutes. This premix phase should be totally clear before addition to the batch.

Step 6

Add the mixture from step #5 to that at Step #4 and mix well for 10 minutes at 10 rpm.

Step 7

In a separate container premix 15.00K of purified water (25.00%) and 2.40K of cromolyn sodium U.S.P. (4.00%) using the Lightnin' mixer at 1750 rpm for 20 minutes and check for uniformity.

Step 8

Add the contents of step #7 to the batch and mix for ½ hour at 20 rpm.

Step 9

Adjust pH to 5.5 with phosphoric acid N.F. if necessary.

Two sets of samples from the top, middle and bottom of the kettle are removed and submitted for cromolyn sodium, methylparaben and propylparaben analysis and other physical tests.

EXAMPLE II

Clinical Trial

A Clinical Trial of the claimed and described process, using the claimed and described composition has been initiated. The trial involves a 3-month treatment period followed by evaluation based on measurement of tumor reduction. No data are currently available.

The foregoing description is intended as illustrative and is not to be taken as limiting. Still other variations within the spirit and scope of this invention are possible and will readily present themselves to those skilled in the art.

I claim:

1. A process for treating hemangioma in a human in need thereof comprising topically administering to said human at the location of the hemangioma a composition comprising a pharmacologically acceptable carrier having dissolved or dispersed therein a therapeutically effective amount of a substituted chromone compound or a pharmacologically acceptable salt, ester or amide thereof, said chromone compound having a structure represented by the formula:

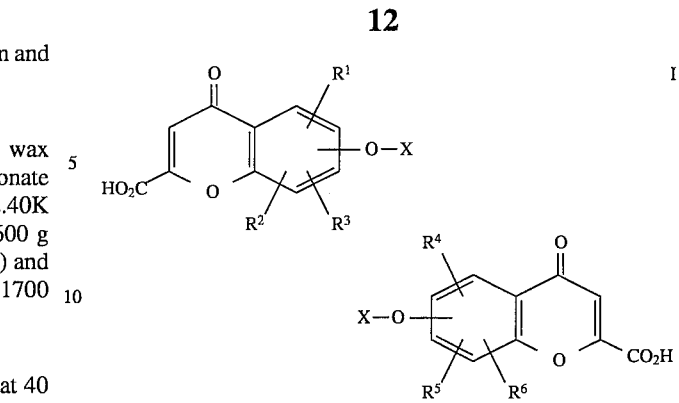

wherein (a) $R^1$, $R^2$, $R^3$, $R^4$, $R^5$, and $R^6$, can each be the same, or different, and each R group is selected from the group consisting of hydrogen, a halo group, a $C_1$–$C_6$ lower alkyl group, hydroxyl, $C_1$–$C_6$ lower alkoxy, substituted $C_1$–$C_6$ lower alkoxy group, and a substituted $C_1$–$C_6$ lower alkyl, where the substituent is selected from the group consisting of a hydroxyl, a lower ($C_1$–$C_6$) alkoxy group, a carboxy group, a halo group, a lower alkenyl group, a benzyl group and nitro group;

(b) the X group can be a straight or branched, saturated or unsaturated hydrocarbon chain having between 3 and 10 carbon atoms, wherein said hydrocarbon chain is optionally interrupted by a substituent selected from the group consisting of oxygen, a carbonyl group, a carbocyclic or heterocyclic ring and can contain a substituent selected from the group consisting of a halo group, a hydroxyl group, and a $C_1$–$C_6$ lower alkoxy group.

2. The process of claim 1 wherein no more than one of said $R^1$, $R^2$ and $R^3$ and no more than one of said $R^4$, $R^5$ and $R^6$ is other than hydrogen wherein each said $R^1$–$R^6$ is unsubstituted; and wherein X is a straight or branched hydrocarbon chain that contains 3–7 carbon atoms.

3. The process of claim 1 wherein each of said $R^1$, $R^2$, $R^3$, $R^4$, $R^5$, and $R^6$ is hydrogen and said carboxyl groups are present as alkali metal carboxylate salts.

4. The process of claim 3 wherein X is is a polymethylene chain substituted by one or more hydroxyl groups.

5. The process of claim 1 wherein said carrier contains a penetration enhancer to aid in absorption by the skin of the said substituted chromone compound.

6. The process of claim 1 wherein said administration is repeated a plurality of times.

7. A process for treating hemangioma in a human in need thereof comprising topically administering to said human at the location of the hemangioma a therapeutically effective amount of the compound, 1,3-bis (2-carboxychromon-5-yloxy)-2-hydroxypropane, or a pharmacologically acceptable salt, ester or amide thereof, dissolved or dispersed in a pharmacologically acceptable carrier.

8. The process of claim 7 wherein said compound is administered in an amount of about 40 to about 1,200 milligrams per day.

9. The process of claim 7 wherein said administration is repeated a plurality of times.

10. The process of claim 7 wherein said compound is administered in an amount of about 100 to about 500 milligrams per day.

11. The process of claim 7 wherein said carrier contains a penetration enhancer to aid in absorption, by the skin, of said compound.

* * * * *